United States Patent [19]

Steiner

[11] Patent Number: 5,688,762
[45] Date of Patent: Nov. 18, 1997

[54] METHOD OF TREATING HYPERTENSION USING ANIMAL STOMACH MUCOSA EXTRACT AND ENDOGENOUS PROTEASE-INHIBITOR PEPTIDES

[76] Inventor: Zoltan W. Steiner, Ungerer Str. 19/I/1o5-2, 80802 Munchen, Germany

[21] Appl. No.: 523,912

[22] Filed: Sep. 6, 1995

[51] Int. Cl.⁶ .............................. A61K 38/17; C07K 1/30; C07K 14/00
[52] U.S. Cl. .............................. 514/2; 514/21; 530/350; 530/300; 530/418
[58] Field of Search .................. 514/2, 21; 530/300, 530/350, 418

[56] References Cited

U.S. PATENT DOCUMENTS

| | | | |
|---|---|---|---|
| 4,478,827 | 10/1984 | Haber et al. | 424/177 |
| 5,008,273 | 4/1991 | Schorrenberg et al. | 514/301 |
| 5,134,123 | 7/1992 | Branca et al. | 514/18 |

OTHER PUBLICATIONS

Structural Changes Associated With the Conversion of the Pepsinogen to Pepsin, *Biochemica et Biophysica Acta*, vol. 22, pp. 537–543 (1956) Vunakis et al.

Structural Changes Associated With the Conversion of Pepsinogen to Pepsin, *Biochemica et Biophysica Acta*, vol. 23, pp. 600–605 (1957) Vunakis et al.

Vunkakis et al. 'Structural Changes Associated With the Conversiono F Pepsinogen to Pepsin', Biochemica et Biophysica Acta, vol. 22, pp. 537–543, 1956.

Vunkakis et al. 'Structural Changes Associated With the Conversiono F Pepsinogen to Pepsin', Biochemica et Biophysica Acta, vol. 23, pp. 600–608, 1957.

*Primary Examiner*—Cecilia J. Tsang
*Assistant Examiner*—Anish Gupta
*Attorney, Agent, or Firm*—Roylance,Abrams,Berdo & Goodman,L.L.P.

[57] ABSTRACT

A process of inhibiting the renin angiotensinogen angiotensin mechanism and treating hypertension administers a blood pressure lowering amount of a protease inhibitor peptide obtained by the cleavage of pepsinogen to a mammal. Hypertension is also treated by administering a blood pressure lowering amount of a stomach mucosa extract from animal origin. The extract is obtained under mild conditions in an extracting solvent containing an acidifying agent.

18 Claims, No Drawings

METHOD OF TREATING HYPERTENSION USING ANIMAL STOMACH MUCOSA EXTRACT AND ENDOGENOUS PROTEASE-INHIBITOR PEPTIDES

FIELD OF THE INVENTION

The present invention relates to the pharmaceutical use of stomach mucosa extract and the use of an acid protease inhibitor of animal origin, which are able to block the renin-angiotensinogen-angiotensin enzymatic system when administered to mammals, including humans. The production or generation of Angiotensin II is prevented or diminished, which is manifested physiologically by a decrease of the arterial blood pressure of the mammal by inhibiting this enzymatic mechanism. The invention is further directed to a method for preparing the stomach mucosae extract.

BACKGROUND OF THE INVENTION

Enzymes and hormones are biocatalysts which control the metabolic processes of an organism. As catalysts, enzymes and hormones increase the rate of one or more reactions and function as directive agents for these occurring reactions. They are of essential importance for living cells. In the blood circulation, enzymes are only present in very limited amounts. They are stored in specific cells in an inactive, insoluble form, and are activated in accordance with the metabolic needs of the organism. The inactive form of the stored enzymes, referred to as zymogens, are enzyme precursors. The activation reaction may be schematically represented as follows:

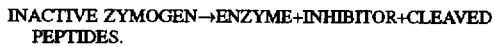

INACTIVE ZYMOGEN→ENZYME+INHIBITOR+CLEAVED PEPTIDES.

The best known example for the activation process is the pepsinogen compound which is converted into pepsin. In the same way prorenin is activated into renin, and proinsulin into insulin. The reversal of the activation process of zymogen is the blocking of the active enzyme by an inhibitor. A typical example of this process is the pepsinogen-pepsin relationship where pepsin is produced by the activation of pepsinogen. The inhibition of pepsin by an inhibitor produces an inactive compound. Other examples with the possible reversibility of the reaction are the enzymes cathepsin, renin, papain and others.

The principle of the inhibition of an enzymatic reaction is based upon the ability of many organic compounds to react with the enzyme protein, either reversibly or irreversibly, and thus, preventing a reaction between the enzyme and the substrate. It follows that the cleaved inhibitor produced during the activation of the zymogen when reunited with the active enzyme should result in the original zymogen.

Examples of previous studies relating to the structure of pepsin and pepsinogen as well as pepsin are disclosed in Vunakis et al., "Structural Changes Associated with the Conversion of Pepsinogen to Pepsin", Biochemica Et Biophysica ACTA, Vol. 22, pp. 537–43 (1956) and Vunakis et al., "Structural Changes Associated with the Conversion of Pepsinogen to Pepsin", Biochemica Et Biophysica ACTA, Vol. 23, pp. 600–5 (1957) which are hereby incorporated by reference.

Numerous chemical compounds have been proposed for blocking the renin angiotensin enzymatic process and thereby controlling or treating hypertension. Examples of related processes are disclosed in U.S. Pat. No. 5,008,273 to Schnorrenberg et al.; U.S. Pat. No. 4,478,827 to Haber et al.; and U.S. Pat. No. 5,134,123 to Branca et al.; which are hereby incorporated by reference.

These processes have met with limited success. Accordingly, there is a continuing need in the art for inhibitor compounds, especially of body own-endogenous origin, controlling the blood pressure mechanism.

SUMMARY OF THE INVENTION

The present invention is directed to use of endogenous enzyme inhibitors, such as those contained in and isolated from the stomach mucosa, or obtained from pepsinogen, which, when administered in pharmaceutically acceptable form to hypertensive mammals, including humans, cause a decrease of arterial blood pressure by preventing or diminishing the occurrence or formation of the vasopressor Angiotensin II compound, which is the cause of high blood pressure. Accordingly, a primary object of the invention is to the use of the protease inhibitor peptide contained in the stomach mucosa extract, by administering an effective amount of the extract to a hypertensive patient or animal, to control their homeostasis.

A further object of the invention is to provide a process for obtaining a hog or chicken stomach extract containing the endogenous pepsin inhibitor peptide, which is capable of reacting with Renin and the ACE-enzyme, to form an inactive prorenin-zymogen and an ACE-zymogen.

The foregoing objects are basically attained by administering a protease inhibitor-peptide containing stomach mucosa extract to an animal to suppress the formation of Angiotensin II, wherein the extract is obtained by forming a paste of minced stomach mucosa, acidifying the paste, precipitating the proteins and extracting with solvents. The resulting extract having a molecular weight of 10.754 with an amino acid content of 101 amino acid residues per mol, namely: 7 Aspartic acid, 10 Glutamic acid, 9 Glycine, 9 Alanine, 8 Valine, 15 Leucine+Isoleucine, 1 Tyrosine, 7 Lysine, 5 Arginine, 2 Methionine, and 3 Histidine residues, is administered to a hypertensive mammal to lower its blood pressure.

These objects are further attained by a process of obtaining a peptide inhibitor extract, comprising the steps of dispersing a comminuted stomach mucosa in a solvent and acidifying the dispersion to a pH of about 2–5.5 to precipitate the proteins and to form a peptide-inhibitor solution, and separating the protein precipitate and recovering the peptide-inhibitor solution.

Other objects, advantages and salient features of the invention will become apparent from the following detailed description which discloses preferred embodiments of the invention.

DETAILED DESCRIPTION OF THE INVENTION

The homeostasis of normal blood pressure in healthy humans is maintained primarily through a regulating system specific for the organism. This self-regulating system establishes an equilibrium between the renin activity and the plasma hormone, angiotensinogen, in such a manner that the production of angiotensin II, the octapeptide responsible for the blood pressure increase, is maintained at acceptably low levels. When an abnormality in the relationship between renin and angiotensinogen occurs, hypertension is a direct consequence.

Renin, an acid protease of the kidney-cortex, is released into the blood plasma from special cells as the renin precursor, prorenin, is activated in response to a variety of stimuli. Renin enters the blood stream by the reaction with the angiotensinogen of the plasma, the so-called "natural substrate". Angiotensinogen is a tetradecapeptide chain having the structure Asp-Arg-Val-Tyr-Ile-His-Pro-Phe-His-Leu-Leu-Val-Tyr-Ser. In the subsequent metabolic process of the renin activity, this tetradecapeptide is cleaved to form the decapeptide Angiotensin I, Asp-Arg-Val-Tyr-Ile-His-Pro-Phe-His-Leu and the tetrapeptide, Leu-Val-Tyr-Ser.

In the next metabolic step, the decapeptide Angiotensin I is further cleaved by the dipeptidyl, hydrolase, or dipeptidyl-carboxypeptidase enzyme. This is often referred to as the Angiotensin I converting enzyme (ACE). In this step, Angiotensin I is converted into the vasopressor octapeptide Angiotensin II, and a neutral dipeptide His-Leu. Angiotensin II is further degraded by anglotensinase to the heptapeptide Angiotensin III, Arg-Val-Tyr-Ile-His-Pro-Phe by the removal of the terminal Aspartic acid group. The heptapeptide Angiotensin III has an undefined physiological function, but is believed to be the mediator for the secretion of the adrenal cortical aldosterol. Angiotensin II and Angiotensin III have a very short half-life and are further cleaved into smaller inactive peptides. Angiotensin II, the most potent endogenous hormone isolated to date, is involved in the blood pressure homeostasis, and indirectly, via mediation of aldosterol released by the adrenal gland, in the regulation of sodium excretion in the kidney. In the normal undisturbed metabolic flow from an initial macro-molecule of the angiotensinogen substrate, an alpha 2-globulin with a mw of 60,000, a decapeptide angiotensin I is cleaved, with a mw of 1900, followed by a further cleavage to the octapeptide angiotensin II with a mw of 1500, and finally to the heptapeptide Angiotensin III with a mw of 1360. The scheme of the angiotensinogen-renin metabolic process is: Natural renin substrate→Tetradecapeptide→Decapeptide/ Angiotensin I→Octapeptide/Angiotensin II→Heptapeptide/ Angiotensin III and Neutral Peptides.

Accompanying the decrease of the molecular weight is a decrease of the negative charges of the amino acid chains. This decrease results in metabolites having fewer negative charges than the original substrate. The metabolic process which generates the vasopressor Angiotensin II can be blocked or inhibited on three sites. First, the generation of Angiotensin II can be inhibited by blocking the activation process of prorenin before the inactive zymogen renin is cleaved into renin. Second, the formation of Angiotensin II can be inhibited by blocking the Leu-Leu position in the tetradecapeptide thereby preventing the formation of the decapeptide Angiotensin I. Third, the formation of Angiotensin II can be inhibited by blocking the activity of the Angiotensin I converting enzyme (ACE) and preventing the formation of Angiotensin II.

A large amount of research has been devoted to the problem of preventing the occurrence of high blood pressure, or alleviating its effects. The research resulted in the discovery of inhibitors able to influence the metabolic process of the renin-angiotensinogen system. Two types of agents that block steps in the generation of Angiotensin II in man have been used, namely, Angiotensin I converting enzyme-inhibitors and Angtotensin I receptor blockers. The third alternative to prevent the activation of prorenin into renin in the glomerular cells was not used.

All these attempts are aimed at blocking the enzyme renin and the ACE-enzyme and thus preventing the reaction between enzyme and substrate. Angiotensin I converting enzyme blockers, such as Teprotide, Captoryl, BRL 36378, Enapryl, etc. block the conversion of the decapeptide, Angiotensin I, into the active Angiotensin II and prevent the degradation of the vasodilating hormone bradykinin. These compounds did not solve the problems of hypertension.

The second group of renin blockers prevents the cleavage of the tetradecapeptide substrate in its Leu-Leu sequence by providing means to inhibit the action of renin upon its natural substrate. This can be achieved by competing with the natural substrate for the active binding site of the substrate. To achieve this aim, compounds of the general formula of: Z-His-Pro-Phe-His-Phe-Phe-X-X-Val-Tyr-Y, with the preferred compound "RIPE"-Pro-His-Pro-Phe-His-Phe-Phe-Val-Tyr/D/-Lis were developed. This substituted D-enantiomorph form is not cleaved by renin. Another group is represented by pepstatin and its derivatives, either of natural or synthetic origin, with the sequences isovaleryl-1 Val-L-Valyl-4 amino-3-hydroxy-6-methylheptanoyl-L-methyl-4 amino-3-hydroxy-6-methyl heptanoic stereoisomers and racemates in substituted alkyl, aryl and cyclo components.

By examining the compounds described, it is apparent that they are all of non-endogenous origin and cannot easily adapt to the complexity of the physiological process occurring in the human organism, especially the complex requirements of the homeostasis control.

Inhibitors derived from the activation of a different zymogen can inhibit the activity of a certain given enzyme. For example, it is apparent that under optimal conditions the pepsin inhibitor compound cleaved from pepsinogen can be reunited with the produced pepsin, resulting in the original pepsinogen-zymogen. There are pronounced similarities between the different acid-proteases, i.e., pepsin, catepsin, renin, proctase, papain, etc., for instance: 1) all have the optimum of activity in ranges of pH 2–4.5, depending on substrate; 2) their activity is inhibited by the activated pentapeptide pepstatin; 3) they all are inhibited by aliphatic diazo-compounds, e.g., diazo-acetyl-D-L-norleucinmethylester; 4) they are not inhibited by the inhibitors EDTA, diisopropyl-phosphofluoride or p-hydromercurobenzoate. One of the important findings of this invention is that the transfer of an acidic protease inhibitor to another acidic protease can take place, transforming it into an inactive zymogen. For instance, the transfer of the pepsin blocking inhibitor can block the activity of the renin enzyme.

The present invention is directed to the discovery that by using the natural regulating mechanism of homeostasis produced by the organisms' metabolism, a blood pressure equilibrium can be achieved by administering compounds of endogenous origin, i.e., compounds existing in healthy animals. This substitutional therapy is achieved by administering an amount of an endogenous enzyme inhibitor to a mammal, including humans, namely the pepsin-inhibitor peptide, to decrease the blood pressure of the subject and prevent or treat hypertension.

The invention is further directed to an improved process for preparing an animal stomach mucosa extract having pepsin and renin inhibiting activity.

The present invention is primarily directed to a method of suppressing the formation of Angiotensin II and treating hypertension in an animal by administering a blood pressure reducing amount of a pepsin-inhibitor peptide-containing extract or a pure pepsin-inhibitor. The peptide-containing extract can be in the form of tablets, coated tablets, capsules, granules, suppositories or solutions. The extract can be administered orally, subcutaneously or parenterally according to standard procedures.

The inhibitor peptide-containing extract is obtained from a number of different sources. In preferred embodiments, the peptide-containing extract is obtained from hog stomach mucosa. In alternative embodiments, the peptide-containing extract is obtained from other animal stomach mucosa including, for example, fowls, such as chickens, turkey or ostrich, and mammals such as cows, dogs, cats and rodents. In still further embodiments, the inhibitor-peptide containing extract can be obtained by esterification, acetylation, condensation and polymerization reactions of the peptides in the extract.

The protease inhibiting peptide-containing extract of this invention contains the pepsin-inhibitor peptide, namely the pepsin and renin inhibitor peptide. The extract is found to inhibit the activity of pepsin and also inhibit the activity of renin thereby inhibiting the renin-angiotensinogen-angiotensin metabolism. This inhibiting effect of the extract suppresses the formation of Angiotensin II and produces a blood pressure lowering effect in humans and other mammals. The blood pressure lowering effect is obtained by the extract blocking the renin angiotensin and Angiotensin I converting enzyme system. The invention is also directed to the discovery that the pepsin inhibitor has an inhibiting effect on pepsin and also renin, thereby causing a blood pressure lowering effect in animals.

The stomach mucosa extract and the pepsin inhibitor peptide affect the renal cells where the extract blocks or inhibits the activation of zymogen prorenin into renin. The stomach mucosa extract also affects the renin activity upon the natural substrate in the circulating plasma by first blocking the Leu-Leu site of the tetradecapeptide, thereby blocking the cleavage of the Angiotensin I decapeptide. The stomach mucosa extract further inhibits the activity of the Angiotensin I Converting Enzyme (ACE), blocking the formation of Angiotensin II from Angiotensin I.

In preferred embodiments, the inhibitor peptide-containing extract is obtained from animal stomach mucosa and, in particular, hog stomach mucosa. The extract is essentially obtained by forming a paste of the minced mucosa, by adding an acidified solvent to precipitate the proteins and dissolve the low molecular weight peptide inhibitor. Generally, the solvent is ethanol acidified to a pH of about 2–5.5. The preferred acidifying acid is hydrochloric acid. The solution is formed from an organic solvent, such as ethanol, or other alcohol, or an aqueous solvent, such as a saline solution. (0.9% sodium chloride in distilled water.)

The acidified supernatant is filtered to recover the filtrate, which then is evaporated to dryness, or to a viscous fluid, and then solubilized in ethanol. The residue is discarded and the filtered solution concentrated by evaporating the solvent under a vacuum to obtain the inhibitor peptide containing extract.

The extraction process is preferably carried out under mild conditions, at a temperature below about 30° C., preferably below 37° C., at a pH of about 2–5.5, and with a salt concentration of about 0–9% sodium chloride. The processing conditions are similar to those found in the body. This produces a pepsin inhibitor peptide extract that is compatible with and stable in the body. The extract can be purified by fractionating by the tungstate precipitation method as known by those skilled in the art.

The obtained stomach mucosa extract has a molecular weight of 10,754 and an average number of 101 amino acid residues per mole as follows:

| Amino Acid | Number of Residues by Chromatography (nearest integer) |
| --- | --- |
| Aspartic acid | 7 |
| Glutamic acid | 10 |
| Glycine | 9 |
| Alanine | 9 |
| Valine | 8 |
| Leucine + Isoleu | 15 |
| Serine | 6 |
| Threonine | 5 |
| Proline | 12 |
| Phenylalanine | 2 |
| Tyrosine | 1 |
| Lysine | 7 |
| Arginine | 5 |
| Methionine | 2 |
| Histidine | 3 |
| Total amino acid residues per mol | 101 |

The stomach mucosa extract obtained by the processes of the invention is stable for extended periods of time when stored at room temperature of about 25° C. Sterilization of the extract at 120° C. has also been shown to have little or no effect on the activity of the extract.

In vivo test results have shown the efficacy of the stomach mucosa extract in lowering blood pressure in a frog's heart, small intestines, dogs (awake and under anesthesia), dogs in long term feeding tests, genetically hypertensive rats, and human volunteer patients. No adverse, toxic or immunological side effects have been observed.

Pure pepsin inhibitor has 29 amino acid residues and a molecular weight of 3242 as determined in Vunakis et al., "Structural Changes Associated with the Conversion of Pepsinogen to Pepsin", Biochemica Et Biophysica ACTA, Vol. 22, pp. 537 (1956). The amino acid residue content of the pepsin inhibitor is as follows.

| Amino Acid | Number of Residues by Chromatography (Nearest Integer) |
| --- | --- |
| Aspartic acid | 4 |
| Glutamic acid | 2 |
| Glycine | 1 |
| Alanine | 2 |
| Valine | 2 |
| Leucine | |
| Isoleucine | 5 |
| Serine | 2 |
| Threonine | 1 |
| Proline | 3 |
| Phenylalanine | 1 |
| Tyrosine | 1 |
| Lysine | 4 |
| Arginine | 1 |
| | 29 |

The pure pepsin inhibitor has also been found to have a blood pressure lowering effect in animals and to suppress the formation of Angiotensin II by blocking or inhibiting the renin-angiotensinogen-angiotensin enzymatic system. In embodiments of the invention, a mixture of the inhibitor peptide containing extract and pure pepsin peptide is administered to the animal. The preferred mixture is a 1:1 mixture by weight.

The inhibitor peptide-containing extract is found to have a blood pressure lowering effect when administered to an animal. The extract inhibits the activity of pepsin and also of renin in complex systems of renin-angiotensinogen.

The dosage of the pepsin-containing extract can vary, depending on the animal and method of administration as recognized by one skilled in the art. By way of experimental data, it has been found that daily oral administration in the range of about 12–12.5 mg/kg of body weight is effective in providing a blood pressure lowering effect. The calculated amount is based on a composition having a ratio of 1:10 of the pepsin-inhibitor containing extract to a pharmaceutically acceptable carrier. Parenteral administration on a daily basis in the amount of about 5 mg/kg of body weight is effective where the amount is a diluted composition of the pepsin-inhibitor containing extract and pharmaceutically acceptable carrier.

The following non-limiting examples depict preferred embodiments of the invention.

EXAMPLE 1

1,000 g fresh stomach mucosa from a recently slaughtered hog was cleaned with lukewarm water to remove solid impurities. The mucosa is then minced using a mincing machine. The resulting paste was mixed with 1,000 ml of 95 Vol % ethanol containing hydrochloric acid to pH 5. The mixture was mixed homogeneously and incubated at 30° C. for 10 minutes, then centrifuged at 1,200 r/min. The supernatant liquid was collected. The remaining solids were extracted twice with the ethanol solvent to improve the recovery yield. The collected liquids were mixed and the alcohol solvent evaporated under vacuum at 100 mmHg, and concentrated to a volume of 300 ml to produce a viscous liquid. 1,000 ml of 95 Vol % ethanol was added to the viscous liquid, and the pH adjusted to pH 5 with hydrochloric acid, while stirring continuously to precipitate the pepsin proteins. The precipitated pepsin proteins were separated by filtration, discarded, and the supernatant liquid evaporated to dryness. The resulting sticky residue was dissolved in 300 ml of 95 Vol % ethanol. To this solution, active charcoal was added, and the resulting solution filtered and liberated from alcohol to a dry consistency. The residue was twice extracted with isobutyl alcohol to remove lipoids and fats. The alcohol solvent was removed by evaporation and the resulting extract was dissolved in 100 ml physiological grade 0.9% sodium chloride saline. The inhibitory activity of the solution is related to the initial weight of the stomach mucosa and is 1:10. (One gram of extract from 10 g of mucosa.)

The amino acid content and molecular weight of the pepsin inhibitor peptide and the mucosa extract are as discussed above.

EXAMPLE 2

1,000 g fresh hog stomach mucosa from a recently slaughtered hog was cleaned with lukewarm water to remove solid impurities. The mucosa was minced using a mincing machine. The resulting paste was mixed with 1,000 ml of 0.9% sodium chloride solution, adjusted to pH 6.0 using hydrochloric acid, and incubated at 30° C. for three hours. To this paste, minced wood shavings, minced straw and polyethylene granules were added to form a semi-dry mixture. This mixture was placed in linen bags and squeezed in a filter press to recover the extract. The extract was mixed with a 72% solution of ammonium sulfate by adding slowly until no more precipitation occurs. After sedimentation of the precipitate, the mixture is filtered. The filtrate is deionized. The salt free solution is concentrated in vacuo to a viscous fluid. A 0.9% sodium chloride solution was added to the viscous fluid to make 100 ml. This solution, with a standard inhibitory activity of 1:10 in relation to the initial stomach mucosa weight, shows identical characteristics as the extract described in Example 1.

EXAMPLE 3

The extracted fluid obtained by the pressing process of Example 2 is adjusted to pH 5.5 with hydrochloric acid and incubated at 30° C. for three hours. The solution is then passed through a Sephadex affinity chromatography column.

EXAMPLE 4

1 g of commercial grade Pepsinogen was dissolved in 10 ml distilled water and acidified with hydrochloric acid at pH 2.5 at 15° C. for a few minutes. The solution was then made alkaline with 20% sodium hydroxide solution to pH 8.0 and allowed to stand for 15 minutes. The resulting pepsin/pepsin inhibitor peptide complex was acidified to pH 5.5. In this solution, pepsin was precipitated with 95 Vol % ethanol, and the mixture put aside for sedimentation. After the separation of the pepsin precipitate by filtration, the resulting solution was passed through an anionic resin column. The acidic and neutral fractions were discarded. The basic peptides adhering to the column were eluted with 7.2% hydrochloric acid, and the eluate concentrated in vacuo. The inhibitory activity of the peptide was tested by Radioimmunoassay.

| | IN VIVO TESTS Example 5 | | | | |
|---|---|---|---|---|---|
| | | Minutes After | | | |
| | Initial MAP | Administration | | | |
| The effect of hog stomach extract 1:10/of exam.1/upon main arterial blood pressure/MAP/ Applied: 2 ml | 173 | 5 99 | 10 149 | 1 150 | 4 146 | 2 1 |
| The effect of pepsin inhibitor peptide/ Ex.4/upon main art. blood pressure Applied: 1.5 ml | 170 | 100 | 136 | 155 | 170 | 1 |
| The effect of stomach mucosa extract upon MAP in essential hypertensive volunteers Total administered Hog stomach mucosa extract: | 210 | After 3 days 180 mmHg After 7 days 170 mmHg After 4 wks. 160–162 mmHg 250 mg/kg body weight | | | | |

EXAMPLE 6

In this example, the blood pressure lowering effects of the extract obtained from Example 1 are analyzed using genetically hypertensive rats. A saline solution containing 10% of the extract (1:10) was prepared. A 2 ml dose per kg of body weight was administered intravenously to each rat. The rats had an average initial blood pressure of 185 mmHg before administration of the extract-containing solution. After five minutes, the average blood pressure was 105 mmHg, and after four hours the blood pressure was 160 mmHg.

EXAMPLE 7

A group of human volunteer patients suffering from hypertension was used in this study. A saline solution containing 10% of the extract of Example 1 (1:10) was prepared. The solution was administered orally in the amount of 250 mg/kg of body weight over a period of seven days. The treatment scheme was as follows.

| Day | Dosage (mg/kg body weight) |
|---|---|
| 1 | 12.5 |
| 2 | 25.0 |
| 3 | 50.0 |
| 4 | 75.0 |
| 5 | 50.0 |
| 6 | 25.0 |
| 7 | 12.5 |

The patients showed an average blood pressure reduction in the amount of 30–50 mmHg over this seven day period.

While advantageous embodiments have been chosen to describe the invention, it will be understood by those skilled in the art that various changes and modifications can be made therein without departing from the scope of the invention as defined in the appended claims.

What is claimed is:

1. A process for suppressing the formation of Angiotensin II in an animal comprising the steps of obtaining a protease-inhibitor peptide-containing extract, wherein said extract is obtained by forming a suspension of an animal stomach mucosa in an acidified solvent, precipitating proteins and recovering said inhibitor peptide-containing extract, said extract having a molecular weight of 10,754 and 101 amino acid residues per mole, and administering an effective amount of said protease-inhibitor peptide-containing extract to a mammal in need thereof to inhibit the renin-angiotensinogen-angiotensin enzymatic system and to suppress the formation of Angiotensin II.

2. The process of claim 1, wherein said peptide-containing extract is obtained by dispersing comminuted animal stomach mucosa in an acidified alcohol to form a solution and precipitating proteins therein, separating the precipitated proteins and evaporating the alcohol to form a viscous liquid, adding an acidified alcohol to said viscous liquid and to precipitating remaining proteins and recovering the solution containing said inhibitor peptide-containing extract.

3. The process of claim 1, wherein said peptide-containing extract is obtained by dispersing comminuted animal stomach mucosa in a saline solution and acidifying said solution, filtering said dispersion and recovering an aqueous extract from said dispersion and precipitating proteins therefrom, and recovering a liquid filtrate and evaporating said filtrate to form a viscous solution of said inhibitor peptide-containing extract.

4. The process of claim 1, wherein said peptide-containing extract administered to said mammal comprises a pharmaceutically acceptable carrier.

5. The process of claim 1, wherein said peptide-containing extract is administered in the form of a solution, tablet, granular, capsule or suppository.

6. The process of claim 1, wherein said peptide-containing extract is administered subcutaneously, parenterally, or orally.

7. The process of claim 1, comprising acidifying said liquid solution with hydrochloric acid to a pH of about 2–5.5.

8. The process of claim 1, comprising administering said peptide-containing extract orally to said animal at a daily rate of about 12.5 mg per kg of body weight.

9. The process of claim 1, comprising administering said peptide-containing extract parenterally to said animal at a daily rate of about 5 mg per kg of body weight.

10. The process of claim 1, wherein said inhibitor peptide-containing extract has a calculated amino acid composition of 7 Aspartic acid, 10 Glutamic acid, 9 Glycine, 9 Alanine, 8 Valine, 15 Leucine+Isoleu, 6 Serine, 5 Threonine, 12 Proline, 2 Phenylalanine, 1 Tyrosine, 7 Lysine, 5 Arginine, 2 Methionine, and 3 Histidine residues.

11. The process of claim 1 wherein said animal stomach mucosa is selected from the group consisting of hog, chicken, turkey, ostrich, dog, cat and rodent.

12. The process of claim 1, wherein said extract is administered to said animal in an amount to induce a blood pressure lowering effect to said animal.

13. The process of claim 1, wherein said solvent is an alcohol or an aqueous saline solution.

14. The process of claim 1, further comprising the steps of evaporating said solvent from said peptide-inhibitor solution to form a viscous solution, and dispersing said viscous solution in a saline solution.

15. A process for suppressing the formation of Angiotensin II within a mammal, the process comprising the step of administering an effective amount of a pepsin-inhibitor-peptide to said mammal to inhibit the renin-angiotensinogen-angiotensin mechanism in said animal and to suppress formation of Angiotensin II, wherein said pepsin-inhibitor peptide has 29 amino acid residues and a molecular weight of about 3242.

16. The process of claim 15 wherein said pepsin-inhibitor-peptide is administered in an amount to induce a blood pressure lowering effect in said mammal.

17. The process of claim 15, comprising administering said pepsin-inhibitor-peptide parenterally to said mammal, at a daily rate of about 5 mg per kg of body weight.

18. The process of claim 15 comprising administering said pepsin-inhibitor-peptide orally to said mammal at a scheme of:

| Day 1 | 12.5 mg |
|---|---|
| Day 2 | 25.0 mg |
| Day 3 | 50.0 mg |
| Day 4 | 50.0 mg |
| Day 5 | 25.0 mg |
| Day 6 | 12.5 mg, | wherein said amounts are per kg of body weight of said mammal.

* * * * *